United States Patent [19]

Gönczi et al.

[11] Patent Number: 4,599,428
[45] Date of Patent: Jul. 8, 1986

[54] PROCESS FOR THE PREPARATION OF 5(6)-THIO SUBSTITUTED BENZIMIDAZOLES

[75] Inventors: Csaba Gönczi; Dezsö Korbonits; Endre Pálosi; Pál Kiss; Gergely Héja; Judit Kun; Mária Szomor née Wundele; Ida Szvoboda née Kanzel; Ede Márványos; Károly Horváth; Vera Kovács née Mindler; Livia Nagy née Korányi, all of Budapest, Hungary

[73] Assignee: Chinoin Gyogyszer es Vegyeszeti Termekek Gyara RT, Budapest, Hungary

[21] Appl. No.: 591,767

[22] Filed: Mar. 21, 1984

Related U.S. Application Data

[60] Division of Ser. No. 458,266, Jan. 17, 1983, Pat. No. 4,473,697, which is a continuation of Ser. No. 259,544, May 1, 1981, abandoned, which is a division of Ser. No. 198,150, Oct. 17, 1980, abandoned.

[30] Foreign Application Priority Data

| Oct. 19, 1979 [HU] | Hungary | CI 1975 |
| Mar. 19, 1980 [HU] | Hungary | 635/80 |
| Apr. 22, 1980 [HU] | Hungary | CI 1975 |
| Jun. 3, 1980 [HU] | Hungary | 1387/80 |
| Jul. 11, 1980 [HU] | Hungary | CI 1975 |
| Sep. 17, 1980 [HU] | Hungary | 835/80 |

[51] Int. Cl.[4] .................. C07D 235/30; C07D 235/32
[52] U.S. Cl. .................................................... 548/306
[58] Field of Search .................................................... 548/306

[56] References Cited

U.S. PATENT DOCUMENTS 3,929,821  12/1975  Beard et al. ..................... 548/306

FOREIGN PATENT DOCUMENTS 1573072  8/1980  United Kingdom .

OTHER PUBLICATIONS

Imidazole and its Derivatives, Part I, Hofmann, Klaus, pp. 249, 254, 255, and 279, Interscience Publishers, New York 1953.
Benzimidazoles and Congeneric Tricyclic Compounds, Part I, Preston, P. N., pp. 87–89 and 332–333, Interscience Publishers, New York.
Chemical Reviews, Shriner, Ralph L., vol. 49, pp. 10 and 78–80, Williams & Wilkins Co., Baltimore, 1951.

Primary Examiner—Henry R. Jiles
Assistant Examiner—Bernard I. Dentz
Attorney, Agent, or Firm—Karl F. Ross; Herbert Dubno

[57] ABSTRACT

A process is disclosed for the preparation of a compound of the formula (XI)

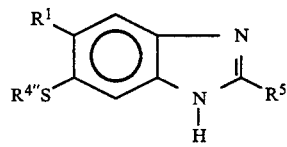

or a salt thereof, wherein
$R^1$ is hydrogen, halogen, $C_1$ to $C_4$ alkyl, $C_1$ to $C_3$ alkoxy, or trifluoromethyl;
$R^5$ is amino or $C_1$ to $C_4$ alkoxycarbonylamino; and
$R^{4''}$ is $C_1$ to $C_6$ alkyl, $C_2$ to $C_6$ alkenyl, $C_2$ to $C_6$ alkynyl, cyclohexyl, benzyl, or 2-phenyl-ethyl, which comprises the steps of:
(a) reacting a compound of the formula (VIII)

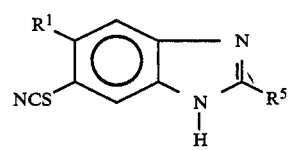

or a salt thereof, with a basic nucleophilic compound to yield a salt of the formula (IX)

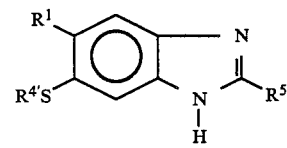

wherein
$R^{4'}$ is a lone pair of electrons, in which case an alkali metal or alkali earth metal cation forms a salt with the sulfur atom; and
(b) reacting a salt of the formula (IX) with a compound of the formula (X)

$R^{4'}$—Q wherein
Q is hydroxyl, halogen, $\frac{1}{2}SO_4$, $\frac{1}{3}PO_3$, $SO_3C_6H_5$, or $SO_3C_6H_4CH_3$ to yield the desired product.

11 Claims, No Drawings

PROCESS FOR THE PREPARATION OF 5(6)-THIO SUBSTITUTED BENZIMIDAZOLES

This application is a division of application Ser. No. 458,266 filed Jan. 17, 1983, now U.S. Pat. No. 4,473,697, which was a continuation of Ser. No. 259,544 filed May 1, 1981 now abandoned, which was a division of Ser. No. 198,150 filed Oct. 17, 1980 now abandoned.

The present invention relates to benzimidazole derivatives and a process for the preparation thereof.

The compounds of the present invention correspond to the Formula

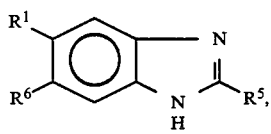

wherein
$R^1$ is hydrogen, halogen, $C_{1-4}$ alkyl, $C_{1-3}$ alkoxy or trifluoromethyl;
$R^5$ is amino or $C_{1-4}$ alkoxycarbonylamino;
$R^6$ is thiocyanato or a group of the Formula —S—$R^4$, in which
$R^4$ is a lone pair of electrons, in which case a metal cation, preferably an alkali metal or alkaline-earth metal cation forms a salt with the sulfur atom; or $R^4$ is hydrogen, a metal atom, preferably an alkali metal or alkaline earth metal atom, or a $C_{1-6}$ alkyl, $C_{2-6}$ alkenyl, $C_{2-6}$ alkinyl, cyclohexyl, benzyl or the 2-phenyl-ethyl group.

The present invention covers the acid addition salts of the above compounds as well.

The compounds of the Formula I, wherein $R^5$ stands for amino, and salts thereof are new.

Compounds of the Formula I exhibit anthelmintic effect and can be useful intermediates in the preparation of compounds having valuable pharmaceutical properties.

There is not known any process on an industrial scale for the preparation of compounds of the Formula I, wherein $R^6$ is a thiocyanato group. A process for the preparation of such compounds is described in Hungarian Patent Specification No. 169.272. According to this process 5(6)-thiocyanato-2-methoxycarbonylaminobenzimidazole is prepared by reducing 1-amino-2-nitro-4-thiocyanato-benzene with a large excess of stannous(II)-chloride in concentrated hydrochloric acid at a temperature of −40° C., extracting the 1,2-diamino-4-thiocyanatobenzene thus formed from the reaction mixture with chloroform and reacting the same in aqueous acetic acid is medium with 1,3-bis-(methoxycarbonyl)-S-methyl-isothio-urea under the development of mercaptane. The disadvantage of this process resides in the use of expensive agents [stannous(II)chloride and 1,3-bis-(methoxycarbonyl)-S-methyl-isothiourea] and the process represents a substantial risk of environmental pollution. Due to the above drawbacks the process is not feasible on industrial scale.

The direct rhodanation of 2-benzimidazole-carbamates of the Formula II was also not known hitherto. Although in the prior art the rhodanation of various heterocyclic compounds is disclosed [S. Patai: "The Chemistry of Cyanates and their Thio Derivatives" Part 2. page 837 (1977); Wiley: Pharmazie, 32 (4), 195 (1977)], benzimidazole derivatives were not subjected to rhodanation reactions. Not even halogenation—which is chemically related to rhodanation—of 2-benzimidazole-carbamates has been described in the prior art. Although the halogenation of 2-substituted benzimidazoles belonging to an other type of compounds was disclosed, the halogenation always resulted in the formation of a mixture of various products e.g. 4(7)-halogeno- and 4,6(5,7)-dihalogeno-benzimidazoles.

It has been found that the 5(6)thiocyanato-benzimidazolylcarbamates of the Formula I may be prepared in highly pure form and with excellent yields by means of selective rhodanation by reacting a compound of the Formula II

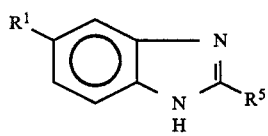

with gaseous chlorine and a rhodanide of the Formula III $$R—SCN \qquad (III)$$

(in which Formulae $R^1$ and $R^5$ are as stated above and R stands for a metal atom or an ammonium group).

According to a preferred embodiment of the process the rhodanating agent chlororhodane prepared by reacting a rhodanide of the Formula III with gaseous chlorine. Preferably the chlororhodane is prepared by reacting a rhodanide of the Formula III with chlorine gas in an anhydrous organic solvent and adding the reaction mixture thus obtained to the solution of a compound of the Formula II and an organic solvent. Alternatively, one can naturally add the solution of the compound of the Formula II to the solution of the chloro rhodane.

The process may be also effected by introducing chlorine gas into a previously prepared solution or suspension of a compound of the Formula II and a compound of the Formula III with an organic solvent. In the latter case the in situ nascendi formed chloro rhodane enters into reaction with the compound of the Formula II.

According to the above reaction variant of the process of the present invention the molar ratio of the compound of the Formula II and the chloro rhodane amounts to 1:1–1:5 and is preferably 1:1–1:3.

According to another preferred embodiment of this variant of the process of the present invention to a solution of 1 mole of a compound of the Formula II formed with an anhydrous organic solvent or solvent mixture 1–3 moles of a rhodanide of the Formula III are added, whereupon 1–4 moles of anhydrous gaseous chlorine is introduced into the solution thus formed at a temperature between 15° C. and 40° C.

The chlorine gas can be added to the solution or suspension of the compounds of the Formulae II and III in the form of a solution formed with an organic solvent as well. The chlorine gas or the solution thereof is preferably added within a short time.

As the rhodanide of the Formula III preferably an alkali metal rhodanide, an alkaline earth metal rhodanide, a heavy metal rhodanide or ammonium rhodanide, preferably potassium, sodium or ammonium rhodanide can be used.

As organic solvent and/or diluent preferably dipolar aprotic solvents can be used in which the components are readily soluble, such as dimethyl formamide, dimethyl sulfoxide, hexamethyl phosphoric acid triamide, lower carboxylic acids, esters, preferably acetates or formiates; $C_{1-4}$ alcohols, chlorinated hydrocarbons preferably chloroform, dichloro methane, tetrachloromethane, or dichloroethane, or nitromethane or acetonitrile.

The reaction temperature falls within the range of 0°–100° C. and amounts preferably to 15°–40° C.

As already mentioned above the known process for the preparation of 5(6)-thiocyanato-benzimidazolyl derivatives described in Hungarian Patent Specification No. 169.272 is accompanied by serious difficulties. The said complicated method was needed for the reduction of the nitro group and the formation of the benzimidazole ring because it was known from prior art that the thiocyanato group was highly reactive and apt to undergo various transformations. From thiocyanates both in alkaline and acidic medium in addition to other products, disulfides and thiol-compounds and mixtures of the said compounds are formed as well [Houben-Weyl: Methoden der organischen Chemie, Reviews 49, 77 (1951)]. It thus could not be foreseen that the nitro group could be selectively reduced by using the conventional methods without simultaneous transformation of the thiocyanato group, because it was known that the said thiocyanato is highly sensitive towards reducing agents and one has to expect the formation of thiols and disulfides. Catalytic hydrogenation of the nitro group in neutral medium could not be taken into consideration, irrespective of the side reactions because the thiocyanato group is a strong catalyst poison.

It has now been found surprisingly that the 5(6)-thiocyanato-benzimidazolyl derivatives of the Formula I can be prepared by a very simple method feasible on industrial scale in high yields by subjecting a compound of the Formula IV

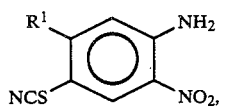

(wherein $R^1$ is as stated above) to selective reduction with iron in neutral or mildly acidic medium in an aqueous-organic heterogenous solvent system and reacting the compound of the Formula V

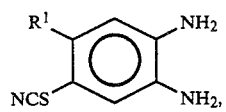

thus obtained (wherein $R^1$ is as stated above) in an aqueous or aqueous-organic solvent system in the presence of an inorganic acid with a cyanamide of the Formula VI $$R^7-NHCN \qquad (VI),$$

(wherein $R^7$ is hydrogen or a $C_{1-4}$ alkoxycarbonyl) at elevated temperature, or in an organic solvent with a halogenocyan of the Formula VII $$HlgCN \qquad (VII),$$

(wherein Hlg is chlorine or bromine).

The present invention is based on the recognition that according to the above variant of the process claimed the reduction of the nitro group takes selectively place and the thiocyanato group is influenced neither by reductive nor by hydrolytic transformation. Thus the use of expensive reactants can be eliminated and there is no need to work at extremely low temperatures. It has been found further that the thiocyanato group is not decomposed even by heating in a relatively strong acidic medium and therefore the benzimidazole ring can be formed without the use of the disadvantageous 1,3-bis-(alkoxycarbonyl)-S-methyl-isothiourea.

According to a preferred embodiment of the reaction the nitro group is reduced by using 2,25–3,5 g-atoms of iron. It is preferred to use iron in finely distributed form. One may proceed preferably by subjecting the iron to pre-treatment with 0.005–0.2 mole of an acid or a salt. The said pretreatment is carried out advantageously between room temperature and 100° C., preferably between 90° C. and 95° C.

As the acid preferably sulfuric acid can be used or hydrochloric acid, while the salt preferably is ammonium chloride, ferrous(II)sulfate, ferric(III)chloride, ammonium sulfate or calcium chloride. The reaction medium used depends on the solubility of the starting materials and may be a water-miscible organic solvent, preferably acetone, dioxane, lower alcohols, or water, preferably methanol. The temperature of the reduction may be 20°–100° C. One may work advantageously at the boiling point of the reaction mixture. The reaction time depends on the starting materials and the reaction conditions and may vary between some minutes and 1-2 hours. It is preferred to select the amount of the acid or the salt and the reaction conditions in such a manner that the reaction time should be between 15 and 60 minutes.

The reaction of the compounds of the Formulae V and VI is carried out preferably in an aqueous acidic medium. The pH of the reaction mixture amounts to 2-6, preferably 3-4. One may proceed preferably by maintaining the pH of the solution at the desired acidic value in the course of the cyclization by adding an aqueous acid to the solution. The reaction temperature amounts to 25°–100° C., and may be preferably 70°–100° C. As acid one may use an organic or inorganic acid preferably hydrochloric acid or sulfuric acid. The reaction is preferably carried out by dissolving a compound of the Formula V in an aqueous acid, preferably in 5N hydrochloric acid. With warming and admixing the solution thus obtained with an aqueous solution of a calcium salt of a compound of the Formula VI.

One may also proceed by omitting the isolation of the calcium salt of the carbalkoxycyanamide of the Formula VI and subjecting to ring closure a carbalkoxycyanamide calcium salt in situ prepared by reacting calcium cyanamide of technical grade with a chloro alkyl formate. According to a preferred embodiment of this process a thiocyanato-orthophenylene-diamine of the Formula V is dissolved in a mixture of water and an organic solvent, preferably ethanol, and reacted with the cyanamide of the Formula VI.

The reaction of the compound of the Formula V and the halogeno cyane of the Formula VII is preferably carried out in a suitable organic solvent, such as lower alcohols, e.g. methanol, ethanol or isopropanol, preferably ethanol, at a temperature between 0° C. and 40° C. On treating the reaction mixture with an alkali hydroxide (preferably sodium or potassium hydroxide) or an alkali carbonate (e.g. sodium or potassium carbonate) a 5(6)-thiocyanato-benzimidazolyl-derivative of the Formula I is obtained.

By preparing the 5(6)-thiocyanato-benzimidazolyl derivatives according to the process of the present invention the drawbacks of the known methods can be overcome. In the process of the invention very cheap starting materials available in large quantities are used and the desired 5(6)-thiocyanato-benzimidazolyl derivatives are obtained in excellent yields.

According to the present invention there is also provided a process for the preparation of compounds of the Formula I, wherein $R^6$ is a group of the Formula $—S—R^4$ and $R^1$, $R^5$ and $R^4$ have the same meaning as stated above.

Compounds of the Formula I, wherein $R^6$ is a group of the Formula $—S—R^4$ and $R^5$ represents an alkoxycarbonylamino group, are known. The majority of the said compounds possess useful anthelmintic properties and can be used in human and verterinary therapy as anthelminitic agents. Other representative of the said compounds are useful intermediates in the preparation of the above end-products.

Compounds of the Formula I, wherein $R^6$ is a group of the Formula $—SR^4$ and $R^5$ represents an alkoxycarbonylamino group, may be prepared according to methods described e.g. in U.S. Pat. Nos. 3,480,642, 3,574,485, 3,915,986, 3,956,499 and 4,152,522 and DE Pat. No. 2,364,351.

According to all of the above procedures compounds of the Formula I, wherein $R^6$ is a group of the Formula $—SR^4$ and $R^5$ represents an alkoxycarbonylamino group, are prepared from a 1,2-diamino-thiobenzene-derivatives bearing a suitable substituent in position 4 by forming the benzimidazole ring. The difference between the above known procedures resides in the fact that the 1,2-diamino-4-thiobenzene derivatives bearing a suitable substituent in position 4 are prepared by different methods.

In U.S. Pat. Nos. 3,915,986 and 3,956,499 a formation of thioethers is described wherein 2-acetamido-4-chloro-nitro-benzene is reacted with toxical alkyl mercaptanes having a very disagreable odor. The 2-acetamido-4-alkylthio-nitro-benzene thus obtained is converted into the 1,2-diamino-4-alkylthio-benzene by hydrolysis and reduction. The 2-acetamido-4-chloro-nitro-benzen is prepared by nitrating m-chloro-acetanilide, whereby the desired product must be separated from the 3-chloro-4-nitroacetanilide formed as by-product [J. Org. Chem. 12, 799 (1947)]. The said reaction can be generally carried out but with low yields [J. Org. Chem. 42, 554 (1977)].

According to another known process 1,2-diamino-4-alkylthio-benzene derivatives are prepared by rhodanating aniline, subjecting the 4-thiocyanato-aniline thus obtained to acetylation, nitrating the 4-thiocyanato-acetanilide thus obtained, subjecting the 2-nitro-4-thiocyanato-acetanlidie thus obtained to selective reduction and alkylation and finally hydrolysing and reducing the product thus obtained. [Ber. 59, 1960/1926/; J. Chem. Soc. 1928, 1364; DE-PS No. 2,363,351.]

In order to avoid the above multi-step process an alternative method has been recently described for the preparation of 1,2-diamino-4-thiocyanato-benzene (U.S. Pat. No. 4,152,522). According to the latter process 4-thiocyanato-2-nitro-aniline, prepared by rhodanating o-nitro-aniline, is used as starting material. The 4-thiocyanato-2-nitro-aniline is reacted with an alkali cyanide and an alkyl halide and the 4-alkylthio-2-nitro-aniline thus obtained is reduced to yield the desired 1,2-diamino-4-thiocyanato-benzene.

The essential feature of the above process is that the alkylthio group is introduced prior to the formation of the benzimidazole-alkyl-carbamate ring but is sensitive to various chemical effects.

According to the process described in DE-OS No. 2,820,375 the alkylthio group is formed in the last step by reduction of the corresponding bis-benzimidazole-disulfide and subsequent alkylation.

It is known from the prior art and from some of the patent specifications referred to above that in some cases the thiocyanato group can be converted into an alkylthio group.

This conversion, however, can be carried out only in some specific cases and special reaction conditions are required, since by-products—primarily disulfides—can be easily formed. This method can not be used if groups liable to hydrolysis are also present in the molecule.

According to DE-PS No. 2,363,351 1-acetamino-2-nitro-4-thiocyanato-benzene is reacted with potassium hydroxide and propyl bromide in methanol at a temperature between 18° C. and 20° C. In this case, however, the formation of the propylthio group can only be carried out beside the hydrolysis of the acetyl group and therefore the amino group must be subjected to acylation again. According to a novel process (U.S. Pat. No. 4,152,522) in the above reaction potassium hydroxide is replaced by alkali or alkaline earth cyanides in order to provide less aggressive reaction conditions.

It is noteworthy that although several methods were disclosed for the preparation of the above compounds and moreover thiocyanato-benzimidazolyl-carbamates were known from DE-PS No. 2,363,351 mentioned above, the conversion of the thiocyanato group of benzimidazolyl-alkylcarbamates—being sensitive to hydrolysis—into an alkylthio group has not been carried out so far.

It has been surprisingly found that compounds of the Formula I, wherein $R^6$ is a group of the Formula $-SR^4$, can be prepared in a simple manner, with excellent yields and in highly pure form by reacting a compound of the Formula VIII

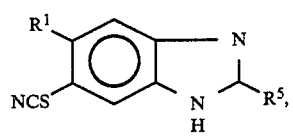
(VIII)

(wherein $R^1$ and $R^5$ are as stated above) with a basic nucleophilic compound and if desired reacting the compound of the Formula IX

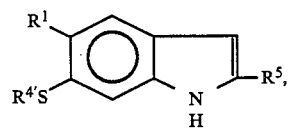
(IX)

thus obtained (wherein $R^1$ and $R^5$ are as stated above and $R^{4'}$ is a lone pair of electrons, in which case an alkali metal or alkaline earth cation forms a salt with the sulfur atom or $R^{4'}$ is hydrogen or a metal atom, preferably an alkali or alkaline earth metal atom) with an alkylating agent of the Formula X $$R^{4''}-Q \qquad (X),$$

(wherein $R^{4''}$ is $C_{1-6}$ alkyl, $C_{2-6}$ alkenyl, $C_{2-6}$ alkinyl, cyclohexyl, benzyl or 2-phenyl-ethyl and Q is halogen, hydroxy, $\frac{1}{2}$ SO$_4$, $\frac{1}{3}$ PO$_3$, $\frac{1}{3}$ PO$_4$, SO$_3$C$_6$H$_5$ or SO$_3$C$_6$H$_4$CH$_3$).

According to further feature of the present invention there is provided a process for the preparation of compounds of the Formula I, wherein $R^6$ is a group of the Formula $-SR^4$ and $R^1$, $R^5$ and $R^4$ are as stated above, and salts thereof, which comprises
(a) reacting a compound of the Formula VIII with a basic nucleophilic compound and if desired alkylating the compound of the Formula IX thus obtained with an alkylating agent of the Formula X, or
(b) for the preparation of compounds of the Formula XI

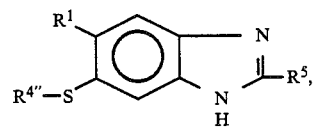
(XI)

(wherein $R^1$, $R^5$ and $R^{4''}$ are as stated above) reacting a compound of the Formula VIII with a basic nucleophilic agent and an alkylating agent of the Formula X; or
(c) for the preparation of compounds of the Formula XI, reacting a mixture of a compound of the Formula VIII and a compound of the Formula X with a basic nucleophilic compound; and if desired converting a compound of the Formula I thus obtained into a salt thereof.

As basic nucleophilic agent one may use preferably an organic or inorganic base, such as an alkali metal or alkaline earth metal hydroxide, an alkali or alkaline earth metal carbonate, an alkali or alkaline earth metal alkoxide or aryloxide, ammonium hydroxide, a tertiary amine, an alkali or alkaline earth metal azide, an alkali or alkaline earth metal cyanide or preferably an alkali or alkaline earth metal sulfide or hydrogen sulfide, particularly preferably sodium sulfide.

As alkylating agent of the Formula X $C_{1-3}$ alcohols, alkyl halides, preferably alkyl bromides; or alkyl sulfates, alkyl phosphites, alkyl phosphates or benzene sulfonic acid esters or p-toluene-sulfonic acid esters may be used.

The reaction may be preferably carried out in the presence of water and/or an organic solvent. One may use water-miscible organic solvents, preferably $C_{1-3}$ alcohols (e.g. methanol, ethanol, isopropanol, n-propanol), acetone dioxane, dimethyl formamide, pyridine, dimethyl sulfoxide or a mixture of such solvents. The reaction may also be effected in water and a water-immiscible organic solvent in the presence of a phase transfer catalyst (e.g. tetrabutyl ammonium chloride, trimethyl benzyl ammonium chloride or triethyl benzyl ammonium chloride etc.).

The reaction temperature may be between 0° C. and the boiling point of the reaction mixture, preferably 10°–40° C. If an alcohol is used as alkylating agent, one may preferably work at 80°–100° C.

According to a preferred embodiment of this process the reaction of the compounds of the Formula VIII, the alkylating agent of the Formula X and the basic nucleophilic agent is carried out in the same reaction vessel.

One may also proceed by admixing the compound of the Formula VIII with the alkylating agent of the Formula X and adding the basic nucleophilic compound to the mixture obtained.

It is expedient to use the compound of the Formula VIII and the basic nucleophilic agent in equimolar amount. This embodiment of the process provides the desired products in almost quantitative yields without any side reactions. If the components are used in stochiometric amounts the undesired effects of the sulfide and those of the rhodanide ions formed are avoided. No disulfides or other by-products are formed and the alkyl carbamate group does not suffer any chemical transformation.

The salts of the compounds of the Formula I may be acid-addition salts formed with inorganic or organic acids conventionally used in such salt formation reactions (e.g. hydrochloric acid, hydrogen bromide, sulfuric acid, nitric acid, maleic acid, fumaric acid, lactic acid, tartaric acid). The salt formation may be carried out by methods known per se.

The process of the present invention has several advantages over the known methods; it is suitable for industrial scale production too, very cheap starting materials available in large amounts are used and the process does not involve risks of environmental pollution.

Further details of the present invention are to be found in the Examples without limiting the scope of protection to the Examples. The term "propyl" and "butyl" means "n-propyl" and "n-butyl", unless otherwise stated.

EXAMPLE 1

Into a solution of 5 g. of 2-(methoxycarbonylamino)-benzimidazole and 7.5 g. of anhydrous potassium rhodanide 5.5 g. of anhydrous gaseous chlorine are introduced. The reaction mixture is diluted with 100 ml. of water and the pH of the solution is adjusted to 4 by adding a 5N sodium hydroxide solution. The precipitated product is filtered off, washed with water and dried at 60° C. Thus 5.6 g. of 5(6)-thiocyanato-2-(methoxycarbonylamino)-benzimidazole are obtained. M.p.: 252°–254° C. (decomposition). Yield: 90%.

EXAMPLE 2

A solution of 7.5 g. of anhydrous potassium rhodanide and 60 ml. anhydrous acetic acid is added at 10°–15° C. under stirring to 70 ml. of carbon tetrachloride containing 5.32 g. of chlorine. The reaction mixture is stirred for a further period of 15-minutes, whereupon a solution of 5 g of 2-(methoxycarbonylamino)-benzimidazole and 25 ml. of anhydrous acetic acid is added. The reaction mixture is stirred at room temperature and poured into water. The carbon tetrachloride layer is separated, the aqueous solution is clarified with activated charcoal and its pH is adjusted to 4 by adding a 5N sodium hydroxide solution. The precipitated product is filtered off, washed with water and dried at 60° C. The 5(6)-thiocyanato-2-(methoxycarbonylamino)-benzimidazole thus obtained melts at 248°–250° C. (decomposition).

EXAMPLE 3

63 g. of iron powder are activated by heating with a mixture of 12 ml of 5N hydrochloric acid and 30 ml. of water on a water bath for half an hour, addition of 270 ml. of water and cooling the suspension to 45° C. follows. A hot solution of 58.5 g. of 4-thiocyanato-2-nitroaniline and 180 ml. of 96% ethanol is added under stirring to the suspension formed. The temperature of the reaction mixture rises slowly. When the temperature reaches 75° C. the reaction mixture is cooled with ice in order to maintain the internal temperature below 85° C. The exothermic stage of the reaction lasts for 3–4 minutes. The reaction mixture is then heated to boiling until no more starting material can be detected by means of thin layer chromatography (about 15 minutes). The warm reaction mixture is filtered, 225 ml. of hot water are added to the filtrate, the solution is clarified with activated charcoal, filtered until warm and the filtrate is allowed to crystallize slowly under stirring. The mixture containing crystals is stirred at 0° C. for 5–6 hours, the crystals are filtered off, washed with cold 25% ethanol and dried in vacuo. Thus 41.6 g. of 4-thiocyanato-1,2-diamino-benzene are obtained, yield: 79%, M.p.: 108°–110° C.

EXAMPLE 4

To a suspension of 2-nitro-4-thiocyanato-aniline, 22.3 g. of powdered iron, 50 ml. of 96% ethanol and 50 ml. of water a solution of 2.2 g. of ammonium chloride and 15 ml. of water is added dropwise under stirring at the boiling point of the mixture. Stirring is continued for a further 15 minutes, whereupon the reaction mixture is filtered until warm. To the filtrate 250 ml. of water are added. After cooling the precipitated crystals are filtered off. Thus 12.2 g. of 4-thiocyanato-1,2-diaminobenzene are obtained. Yield: 74%. M.p.: 108°–110° C.

EXAMPLE 5

To a suspension of 2-nitro-4-thiocyanato-aniline, 22.3 g. of powdered iron, 40 ml. of 96% ethanol and 50 ml. of water a solution of 2,2 g. of ferrous(II)chloride and 4 ml. of water is added dropwise under stirring at the boiling point of the mixture. Stirring is continued for a further 10 minutes, whereupon the reaction mixture is filtered. To the filtrate 200 ml. of water are added. On cooling crystals precipitate, which are filtered off. Thus 12.3 g. of 4-thiocyanato-1,2-diamino-benzene are obtained. Yield: 74.5%. M.p.: 108°–110° C.

EXAMPLE 6

16.5 g. of 1,2-diamino-4-thiocyanato-benzene are dissolved in 20 ml. of 5N hydrochloric acid at 80° C., whereupon the warm solution is added to a solution of 13.7 g. of the calcium salt of carbomethoxy-cyanamide and 50 ml. of water heated to 80° C. within 10 minutes. The temperature of the reaction mixture is raised to 93°–95° C. After the completion of the addition the pH of the solution is controlled and maintained within the range of 3–4, if necessary, by adding 5N hydrochloric acid. After a few minutes the precipitation of crystals begins and the pH is maintained between 3 and 4 by occasional addition of 5N hydrochloric acid. When no more acid is added the reaction mixture is stirred for a further 15 minutes and the precipitated crystals are filtered off, washed successively, with water and hot methanol. Thus 22.4 g. of 5(6)-thiocyanate-2-(methoxycarbonylamino)-benzimidazole are obtained. Yield: 90.5%. According to mass spectrography the molecular weight of the product amounts to 248.

EXAMPLE 7

32 g. of calcium cyanamide of technical grade (which corresponds to 0.22 g. of calcium cyanamide) are stirred vigrorously in 114 ml. of water at 30° C. for an hour, whereupon 20.5 ml. (25.4 g., 0.269 mole) of ethyl chloroformate are added dropwise within half an hour at this temperature. The reaction mixture is stirred for a further hour and the impurities are removed by filtration. The pure filtrate is warmed to 80° C., whereupon a solution of 33 g. (0.20 mole) of 1,2-diamino-4-thiocyanato-benzene in 40 ml. of 5N hydrochloric acid, heated to 80° C., is added. The reaction mixture is worked up as described in Example 6. Thus 41 g. of 5(6)-thiocyanato-2-(methoxycarbonylamino)-benzimidazole are obtained. Yield: 83%. The product is identical with that obtained according to Example 6.

EXAMPLE 8

One proceeds according to Example 7 except that the solution of 1,2-diamino-4-thiocyanato-benzene formed with a mixture of 50 ml. of 5N hydrochloric acid and 40 ml. of 96 & ethanol is added to the solution of the carbomethoxycyanamide. The reaction mixture is worked up as described in Example 7. The 5(6)-thiocyanato-2-(methoxycarbonylamino)-benzimidazole is obtained in the form of nice crystals.

EXAMPLE 9

2.48 g. of 5(6)-thiocyanato-2-(methoxycarbonylamino)-benzimidazole are suspended in 25 ml. of 96% ethanol, whereupon upon 1.25 g. propyl bromide are added. A solution of 2.4 g. of sodium sulfide nonahydrate and 2 ml. of water is added dropwise within half an hour at 20°–25° C. under vigorous stirring. At first a yellow solution is formed, from which the precipitation of crystals begins soon. The product is filtered off, washed and dried. Thus 2.50 g. of 5(6)-propylthio-2-(methoxycarbonylamino)-benzimidazole are obtained. Yield: 94%. M.p.: 212°–213° C.

EXAMPLE 10

124 g. of 5(6)-thiocyanato-2-(methoxycarbonylamino)-benzimidazole are suspended in 1.5 l. of 96% ethanol, whereupon 62.5 g. of propyl bromide are added. A solution of 120 g. of sodium sulfide nonahydrate and 200 ml. of water is added dropwise within half an hour at 20°–25° C. under vigorous stirring. A brown solution is formed, from which the precipitation of crystals begins soon. The product is filtered off, washed with methanol and dried. Thus 127 g. of 5(6)-propylthio-2-(methoxycarbonylamino)-benzimidazole are obtained. Yield: 96%. M.p.: 212°–213° C.

EXAMPLE 11

24.8 g. of 5(6)-thiocyanato-2-(methoxycarbonylamino)-benzimidazole are suspended in 100 ml. of dimethyl sulfoxide, whereupon a solution of 29.0 g. of sodium sulfide nonahydrate and 100 ml. methanol is added dropwise at 20° C. within 3–5 minutes. To the clear faint yellow solution thus formed 15 g. of propyl bromide are added at the same temperature. The precipitation of crystals begins within 1–2 minutes. The mixture is stirred for a further half an hour, whereupon the pH is adjusted to 7 by adding 5N hydrochloric acid. The precipitated crystals are filtered off, washed successively with water and alcohol and dried in vacuo at 60° C. Thus 26.0 g. of 5(6)-propylthio-2-(methoxycarbonylamino)-benzimidazole are obtained. Yield: 98%. M.p.: 214°–215° C.

EXAMPLE 12-23

The compounds enumerated in the following Table are prepared in an analogous manner to the process described in Examples 9–11 by using the corresponding starting materials. In the compounds of the Formula I thus obtained $R^5$ stands for methoxycarbonylamino.

| Example No. | $R^1$ | $R^6$ | Mp. °C. |
| --- | --- | --- | --- |
| 12 | chlorine | n-propylthio | 250 (dec.) |
| 13 | chlorine | benzylthio | 234–236 |
| 14 | chlorine | allylthio | 203–205 |
| 15 | chlorine | propinylthio | 305–307 |
| 16 | chlorine | ethylthio | 237–238 |
| 17 | chlorine | cyclohexylthio | 294–295 |
| 18 | bromine | n-propylthio | 191–193 |
| 19 | methyl | n-propylthio | 234–235 (dec.) |
| 20 | methoxy | n-propylthio | 296–298 |
| 21 | butyl | n-propylthio | 202–204 |
| 22 | trifluoromethyl | n-propylthio | 252 |
| 23 | fluorine | n-propylthio | 252–253 |

EXAMPLE 24

To a solution of 2.48 g. of 5(6)-thiocyanato-2-(methoxycarbonylamino)-benzimidazole and 60 of 85% acetone a solution of 2.9 g. of sodium sulfide nonahydrate in 5 ml. of water is added. After 40 minutes the reaction mixture is clarified and filtered. To the yellow solution thus obtained acetone is added. The precipitated sodium salt of 5(6)-thiol-2-(methoxycarbonylamino)-benzimidazole is filtered off, washed in acetone and dried over potassium hydroxide in vacuo. Yield: 2.3 g.

M.p.: 300°–305° (decomposition).

IR: 1705 $cm^{-1}$ (ester-carbonyl); 3150–2200 $cm^{-1}$ (benzimidazole N); 802 $cm^{-1}$ (1,2,4-trisubstituted benzene).

H-NMR: an exchangeable proton at 6.388 ppm.

Raman-spectrum: a characteristic bond of the SH group at 2555 $cm^{-1}$.

EXAMPLE 25

2.3 g. of the sodium salt prepared according to Example 24 is taken up in 25 ml. of 50% ethanol. The pH of the mixture is adjusted to 5 by adding hydrochloric acid. The precipitated 5(6)-thiol-2-(methoxycarbonylamino)-benzimidazole is filtered off and washed. Yield: 1.56 g., m.p.: 261°–262° C.

Analysis: calculated: N%=18.82; S%=14.36; found: N%=18.30; S%=14.35.

EXAMPLE 26

2.45 g. of the sodium salt of 5(6)-thiol-2-(methoxycarbonylamino)-benzimidazole are suspended in 35 ml. of 65 vol.% acetone. The solution thus obtained is clarified with activated charcoal, filtered, whereupon 1.3 g. of propyl bromide are added at a temperature of 10°–15° C. After half an hour the pH of the mixture is adjusted to 6, the precipitated crystals are filtered off and washed. Thus 2.5 g. of 5(6)-propylthio-2-(methoxycarbonylamino)-benzimidazole are obtained. j M.p.: 214° C. (decomposition).

EXAMPLE 27

2.23 g. of 5(6)-thiol-2-(methoxycarbonylamino)-benzimidazole are dissolved in 30 ml. of 60% ethanol, containing 0.8 g. of sodium hydroxide, whereupon 1.3 g. of propyl bromide are added at a temperature of 10°–15° C. The reaction mixture is stirred for half an hour, whereupon the pH is adjusted to 6 and the precipitated 5(6)-propylthio-2-(methoxycarbonylamino)-benzimidazole is filtered off. Yield: 2.4 g. Mp.: 212°–214° C. (decomposition).

EXAMPLE 28

49.66 g. (0.2 mole) of 5(6)-thiocyanato-2-(methoxycarbonylamino)-benzimidazole are suspended in 600 ml. of 65% aqueous acetone. To the suspension thus obtained a solution of 58 g. (0.24 mole) of sodium sulfide nonahydrate and 100 ml. of water is added within 5 minutes at a temperature between 20° C. and 25° C. A light yellow solution is obtained which contains a small amount of a precipitate. The solution is clarified with 4 g. of activated charcoal, filtered and washed twice with 20 ml. of 65% acetone each. To the clear solution thus obtained a solution of 30 g. (0.24 mole) of propyl bromide and 100 ml acetone is added at 10°–15° C. within 5 minutes. The reaction mixture is stirred for an hour, the pH is adjusted to 6 by adding 5N hydrochloric acid. The mixture is stirred for half an hour, whereupon the precipitated product is filtered off, suspended twice in 60 ml. of 50% by volume acetone each, washed twice with 30 ml. of acetone each and dried. Thus 47.3 g. of 5(6)-propylthio-2-(methoxycarbonylamino)-benzimidazole are obtained in the form of snow while microcrystals. Yield: 89%.

EXAMPLE 29

24.8 g. (0.1 mole) of 5(6)-thiocyanato-2-(methoxycarbonylamino)-benzimidazole are suspended in 300 ml of 65% by volume aqueous acetone under vigorous stirring, whereupon 30 g. of propyl bromide are added. To the suspension thus obtained 22 g. of potassium hydroxide are added at 15° C. in the form of a 40% aqueous solution. After 1–2 minutes a light yellow solution is obtained. The end product of the reaction is determined by means of thin layer chromatography (silicagel G254 plate; solvent mixture: 9:1 mixture of chloroform and acetic acid; developped by UV). After the completion of the reaction (3–4 hours) the pH of the solution is adjusted to 6 by adding 5N hydrochloric acid. The reaction mixture is allowed to stand for a short time, the precipitated crystals are filtered off, washed successively with aqueous acetone and water. Thus 20.5 g. of 5(6)-propylthio-2-(methoxycarbonylamino)-benzimidazole are obtained. M.p.: 210°–212° C.

EXAMPLE 30

One proceeds according to Example 29 except that 70% aqueous ethanol is used in the place of 65% acetone. Thus 19.8 g. of 5(6)-propylthio-2-(methoxycarbonylamino)-benzimidazole are obtained. M.p.: 209°–211° C.

EXAMPLE 31

One proceeds according to Example 29 except that potassium hydroxide is replaced by a 40% aqueous solution of 32 g. of sodium hydroxide. Thus 19.7 g. of 5(6)-propylthio-2-(methoxycarbonylamino)-benzimidazole are obtained. M.p.: 211°–213° C.

EXAMPLE 32

8.25 g. of 2-amino-4-thiocyanato-aniline are dissolved in 60 ml. of acetone, whereupon a solution of 6.1 g. of bromo cyane and 20 ml. of ethanol is added dropwise. The reaction mixture is allowed to stand overnight, whereupon it is evaporated to dryness. The residue is taken up in water and the pH of the solution formed is adjusted to 8 by adding a 2N sodium hydroxide solution. The precipitated crystals are filtered off, washed with water and dried. Thus 8.3 g. of 2-amino-5-thiocyanato-1H-benzimidazole are obtained. M.p.: 204°–205° C. (decomposition).

What we claim is:

1. A process for the preparation of a compound of the formula (IX)

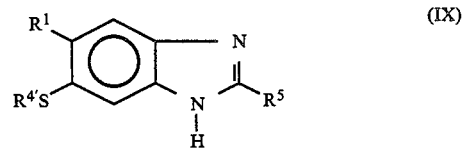

wherein
$R^1$ is hydrogen, halogen, $C_{1-4}$ alkyl, $C_{1-3}$ alkoxy, or trifluoromethyl;
$R^5$ is amino or $C_{1-4}$ alkoxycarbonylamino; and
$R^{4'}$ is a lone pair of electrons, in which case an alkali metal or alkali earth metal cation forms a salt with the sulfur atom, or $R^{4'}$ is hydrogen, or a salt thereof, which comprises the steps of:
(a) reacting a compound of the formula (VIII)

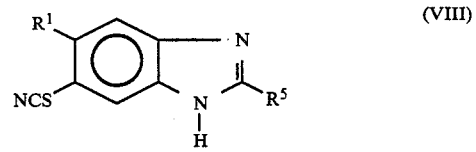

or a salt thereof, with an alkali or alkali earth metal sulfide to yield a salt of the formula (IX) wherein $R^{4'}$ is a lone pair of electrons, and in the case where compounds of the formula (IX) where $R^{4'}$ is hydrogen are to be produced;
(b) acidifying the salt of the formula (IX), prepared during step (a) to yield the desired product.

2. A process for the preparation of a compound of the formula (XI)

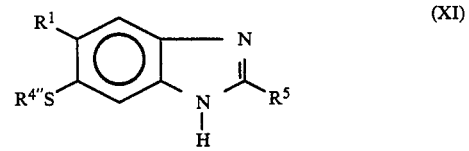

or a salt thereof, wherein
$R^1$ is hydrogen, halogen, $C_1$–$C_4$ alkyl, $C_1$–$C_3$ alkoxy, or trifluoromethyl;
$R^5$ is amino or $C_1$–$C_4$ alkoxycarbonylamino; and
$R^{4''}$ is $C_1$–$C_6$ alkyl, $C_2$–$C_6$ alkenyl, $C_2$–$C_6$ alknynyl, cyclohexyl, benzyl, or 2-phenyl-ethyl, which comprises the steps of:
(a) reacting a compound of the formula (VIII)

$$\underset{\text{NCS}}{\overset{R^1}{\diagup}}\!\!\!\!\!\!\!\!\!\!\!\bigcirc\!\!\!\!\!\!\!\!\!\!\!\underset{\underset{H}{N}}{\overset{N}{\diagdown}}\!\!\!\!\!\!R^5 \qquad \text{(VIII)}$$

or a salt thereof, with an alkali or alkali earth metal sulfide to yield a salt of the formula (IX)

$$\underset{R^{4'}S}{\overset{R^1}{\diagup}}\!\!\!\!\!\!\!\!\!\!\!\bigcirc\!\!\!\!\!\!\!\!\!\!\!\underset{\underset{H}{N}}{\overset{N}{\diagdown}}\!\!\!\!\!\!R^5 \qquad \text{(IX)}$$

wherein
  $R^{4'}$ is a lone pair of electrons, in which case an alkali metal or alkali earth metal cation forms a salt with the sulfur atom; and
  (b) reacting the salt of the formula (IX) with a compound of the formula (X)

$$R^{4''}-Q \qquad \text{(X)}$$

wherein
  Q is hydroxyl, halogen, $\frac{1}{2}SO_4$, $\frac{1}{3}PO_3$, $\frac{1}{3}PO_4$, $SO_3-C_6H_5$ or $SO_3C_6H_4CH_3$ to yield the desired product.

3. A process for the preparation of a compound of the formula (XI)

$$\underset{R^{4''}S}{\overset{R^1}{\diagup}}\!\!\!\!\!\!\!\!\!\!\!\bigcirc\!\!\!\!\!\!\!\!\!\!\!\underset{\underset{H}{N}}{\overset{N}{\diagdown}}\!\!\!\!\!\!R^5 \qquad \text{(XI)}$$

or a salt thereof, wherein
  $R^1$ is hydrogen, halogen, $C_1-C_4$ alkyl, $C_{1-3}$ alkoxy, or trifluoromethyl;
  $R^5$ is amino or $C_1-C_4$ alkoxycarbonylamino; and
  $R^{4''}$ is $C_1-C_6$ alkyl, $C_2-C_6$ alkenyl, $C_2-C_6$ alkynyl, cyclohexyl, benzyl, or 2-phenyl-ethyl, which comprises the step of:
  reacting a compound of the formula (VIII)

$$\underset{\text{NCS}}{\overset{R^1}{\diagup}}\!\!\!\!\!\!\!\!\!\!\!\bigcirc\!\!\!\!\!\!\!\!\!\!\!\underset{\underset{H}{N}}{\overset{N}{\diagdown}}\!\!\!\!\!\!R^5 \qquad \text{(VIII)}$$

or a salt thereof, with an alkali or alkali earth metal sulfide and then with a compound of the formula (X)

$$R^{4''}-Q \qquad \text{(X)}$$

wherein $R^{4''}$ is $C_1-C_6$ alkyl, $C_2-C_6$ alkenyl, $C_2-C_6$ alkynyl, cyclohexyl, benzyl, or 2-phenylethyl and Q is hydroxy, halogen, $\frac{1}{2}SO_4$, $\frac{1}{3}PO_3$, $\frac{1}{3}PO_4$, $SO_3-C_6H_5$, or $SO_3C_6H_4CH_3$ to yield the desired product.

4. A process for the preparation of a compound of the formula (XI)

$$\underset{R^{4''}S}{\overset{R^1}{\diagup}}\!\!\!\!\!\!\!\!\!\!\!\bigcirc\!\!\!\!\!\!\!\!\!\!\!\underset{\underset{H}{N}}{\overset{N}{\diagdown}}\!\!\!\!\!\!R^5 \qquad \text{(XI)}$$

or a salt thereof, wherein
  $R^1$ is hydrogen, halogen, $C_1-C_4$ alkyl, $C_1-C_3$ alkoxy, or trifluoromethyl;
  $R^5$ is amino or $C_1-C_4$ alkoxycarbonylamino; and
  $R^{4''}$ is $C_1-C_6$ alkyl, $C_2-C_6$ alkenyl, $C_2-C_6$ alkynyl, cyclohexyl, benzyl, or 2-phenylethyl, which comprises the step of:
  reacting a compound of the formula (VIII)

$$\underset{\text{NCS}}{\overset{R^1}{\diagup}}\!\!\!\!\!\!\!\!\!\!\!\bigcirc\!\!\!\!\!\!\!\!\!\!\!\underset{\underset{H}{N}}{\overset{N}{\diagdown}}\!\!\!\!\!\!R^5 \qquad \text{(VIII)}$$

or a salt thereof and a compound of the formula (X)

$$R^{4''}-Q \qquad \text{(X)}$$

wherein $R^{4''}$ is $C_1-C_6$ alkyl, $C_2-C_6$ alkenyl, $C_2-C_6$ alkynyl, cyclohexyl, benzyl, or 2-phenylethyl, and Q is hydroxy, halogen, $\frac{1}{2}SO_4$, $\frac{1}{3}PO_3$, $\frac{1}{3}PO_4$, $SO_3-C_6H_5$, or $SO_3-C_6H_4-CH_3$ and with an alkali or alkali earth metal sulfide to yield the desired product.

5. The process defined in claim 1 which comprises using sodium sulfide nonahydrate as the alkali or alkali earth metal sulfide.

6. The process defined in claim 2 which comprises using sodium sulfide nonahydrate as the alkali or alkali earth metal sulfide.

7. The process defined in claim 3 which comprises using sodium sulfide nonahydrate as the alkali or alkali earth metal sulfide.

8. The process defined in claim 4 which comprises using sodium sulfide monohydrate as the alkali or alkali earth metal sulfide.

9. The process defined in claim 2 wherein in step (b) the compound of the formula (X) is a $C_1-C_3$ alcohol, alkyl halide, alkyl sulfate, alkyl phosphate, alkyl phosphite, benzene sulfonic acid ester, or toluene sulfonic acid ester.

10. The process defined in claim 3 wherein the compound of the formula (X) is a $C_1-C_3$ alcohol, alkyl halide, alkyl sulfate, alkyl phosphate, alkyl phosphite, benzene sulfonic acid ester, or toluene sulfonic acid ester.

11. The process defined in claim 4 wherein the compound of the formula (X) is a $C_1-C_3$ alcohol, alkyl halide, alkyl sulfate, alkyl phosphate, alkyl phosphite, benzene sulfonic acid ester, or toluene sulfonic acid ester.

* * * * *